United States Patent [19]

Brown et al.

[11] 4,156,002
[45] May 22, 1979

[54] PHARMACEUTICAL COMPOSITIONS

[75] Inventors: Edward D. Brown; Walter Hepworth, both of Macclesfield; Ian T. Kay, Wokingham, all of England

[73] Assignee: Imperial Chemical Industries Limited, London, England

[21] Appl. No.: 877,391

[22] Filed: Feb. 13, 1978

[30] Foreign Application Priority Data

Feb. 21, 1977 [GB] United Kingdom ............... 7183/77

[51] Int. Cl.$^2$ .................... C07D 251/46; A61K 31/53
[52] U.S. Cl. .................................... 424/249; 544/194; 544/211
[58] Field of Search ................. 544/194, 211; 424/249

[56] References Cited

U.S. PATENT DOCUMENTS

4,035,365  7/1977  Kay ........................... 544/211

Primary Examiner—John M. Ford
Attorney, Agent, or Firm—Cushman, Darby & Cushman

[57] ABSTRACT

The invention concerns pharmaceutical compositions having analgesic, and in some cases, in addition anti-inflammatory properties, for use in the treatment of painful inflammatory joint disease, which compositions contain as active ingredient a new or old 1-alkyl (or cycloalkyl)-4-(N-alkanoyl)substituted-amino-tetrahydro-1,3,5-triazine-2,6-dione of the formula:

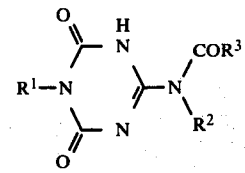

or a base-addition salt thereof.

Many of the compounds of formula I are previously known as herbicides, and a representative example of such a compound which has now been surprisingly found to have useful analgesic properties is 1-isopropyl-4-(N-acetyl)isopropylamino-tetrahydro-1,3,5-triazine-2,6-dione. However certain of the compounds of formula I and the base-addition salts thereof are novel, a representative example being 1-isopropyl-4[(N-acetyl)-pent-3-ylamino]-tetrahydro-1,3,5-triazine-2,6-dione, and are provided as a further feature of the invention, together with analogy processes for their manufacture.

10 Claims, No Drawings

PHARMACEUTICAL COMPOSITIONS

This invention relates to new pharmaceutical compositions and in particular it relates to new pharmaceutical compositions which possess analgesic properties. In addition certain of the compositions also possess anti-inflammatory properties and/or are inhibitors of prostaglandin synthetase.

According to the invention there is provided a pharmaceutical composition which comprises as active ingredient a 1,3,5-triazine-2,6-dione of the formula:

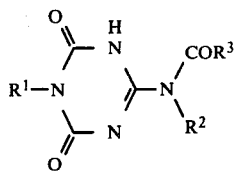

wherein $R^1$ is a $C_{1-6}$-alkyl or $C_{3-6}$-cycloalkyl radical; $R^2$ is a $C_{1-10}$-alkyl radical, a $C_{1-4}$-alkyl radical bearing a $C_{1-4}$-alkoxy radical, a $C_{3-8}$-cycloalkyl or $C_{3-6}$-alkenyl radical, or a phenyl or phenyl-$C_{1-4}$-alkyl radical optionally bearing an aromatic substituent selected from halogen atoms, $C_{1-4}$-alkyl and $C_{1-4}$-alkoxy radicals; and $R^3$ is a $C_{1-4}$-alkyl radical; or a pharmaceutically acceptable base-addition salt thereof; together with a pharmaceutically acceptable diluent or carrier.

It will be appreciated that certain of the compounds of formula I possess at least one asymmetric carbon atom and may therefore exist in racemic and optically active forms, namely those compounds of formula I wherein $R^1$, $R^2$ or $R^3$ is a radical containing an asymmetric carbon atom. It is to be understood that this specification relates to those racemic and optically active forms, of such compounds, which possess the useful properties mentioned hereinbelow, it being well known in the general art how to prepare optically active forms by resolution of the corresponding racemate or by synthesis from optically active starting materials, and how to determine their pharmacological properties by the standard tests described hereinbelow.

A particular value for $R^1$ when it is a $C_{1-6}$-alkyl radical is, for example, a methyl, ethyl, n-propyl, isopropyl, n-butyl, isobutyl, sec-butyl or neopentyl radical; and when it is a $C_{3-6}$-cycloalkyl radical is, for example, a cyclopropyl, cyclobutyl, cyclopentyl or cyclohexyl radical.

A particular value for $R^2$ when it is a $C_{1-10}$-alkyl radical is, for example, a straight chain $C_{1-10}$-alkyl radical, for example a methyl, ethyl, n-propyl, n-butyl or n-pentyl radical, or is a branched chain $C_{3-10}$-alkyl radical, for example an isopropyl, isobutyl, sec-butyl, pent-2-yl, pent-3-yl, neopentyl, hex-2-yl, hex-3-yl or hept-4-yl radicals, of which values, those wherein the linking α-carbon atom is secondary, for example an isopropyl, sec-butyl, pent-2-yl, pent-3-yl, hex-2-yl, hex-3-yl or hept-4-yl radical, are preferred; and a hex-3-yl or pent-3-yl radical are especially preferred.

A particular value for $R^2$ when it is a $C_{3-6}$-alkenyl radical is, for example, an allyl or 2-methylallyl radical; and when it is a $C_{3-8}$-cycloalkyl radical is, for example, a cyclopropyl, cyclobutyl, cyclopentyl, cyclohexyl or norbornyl radical.

A particular value for $R^2$ when it is a $C_{1-4}$-alkyl radical bearing a $C_{1-4}$-alkoxy radical is, for example, a 2-methoxy- or 2-ethoxy-ethyl radical; and when it is a phenyl-$C_{1-4}$-alkyl radical is, for example, a benzyl, 1-(phenyl)ethyl or 2-(phenyl)ethyl radical.

A particular value for an aromatic substituent which may be present when $R^2$ is a phenyl or phenyl-$C_{1-4}$-alkyl radical is, for example:

when it is a halogen substituent, a fluorine, chlorine or bromine atom;

when it is a $C_{1-4}$-alkyl substituent, a methyl radical; and when it is a $C_{1-4}$-alkoxy substituent, a methoxy radical.

Specific values for $R^2$ when it is an optionally substituted phenyl or phenyl-$C_{1-4}$-alkyl radical are, for example, when it is a phenyl, benzyl, 1-(phenyl)ethyl, 2-(phenyl)ethyl, 4-chlorophenyl, 4-methylphenyl, 3-methoxyphenyl and 4-chlorobenzyl radical.

A particular value for $R^3$ is, for example, a methyl, ethyl or n-propyl radical, of which a methyl radical is particularly preferred.

A particular base-addition salt of a compound of formula I is, for example, an alkali metal or alkaline earth metal salt, for example a sodium, potassium, calcium or magnesium salt, an aluminium salt, for example an aluminium hydroxide di-salt, a copper salt or a complex therewith, or a salt with an organic base affording a pharmaceutically acceptable cation, for example triethanolamine or benzylamine.

Particular groups of compounds of formula I which are of special interest as active ingredients comprise those compounds of formula I wherein:

(a) $R^1$ is an isopropyl, n-propyl, sec-butyl, n-butyl or cyclohexyl radical;

(b) $R^2$ is a branched chain $C_{3-10}$alkyl radical wherein the linking α-carbon is secondary;

(c) $R^2$ is a cyclopropyl, isopropyl, isobutyl, sec-butyl, pent-2-yl, pent-3-yl or hex-3-yl radical; or (d) $R^3$ is a methyl radical;

and in each case the remainder of $R^1$, $R^2$ and $R^3$ have any of the general or particular meanings defined hereinabove; together with the pharmaceutically acceptable base-addition salts thereof.

When both $R^1$ and $R^2$ are alkyl radicals as defined hereinbefore, it is preferred that, taken together they number four or more carbon atoms.

The pharmaceutical compositions of the invention may be obtained by conventional means using conventional diluents and carriers, and may be in a form suitable for oral administration, for example in the form of a tablet, capsule, syrup or elixir; or for parenteral administration, for example in the form of a sterile injectable aqueous suspension oily solution or oily suspension; or for rectal administration, for example in the form of a suppository; or for vaginal administration, for example in the form of a pessary.

Compositions intended for oral use may be prepared according to any method known in the art for the manufacture of orally-administrable pharmaceutical compositions, and such compositions may contain one or more agents selected from sweetening agents, for example sucrose, flavouring agents, for example essential oils, and colouring agents, in order to provide an elegant and palatable preparation.

Tablets of the invention may contain the active ingredient in admixture with conventional pharmaceutical excipients. Suitable pharmaceutical excipients are, for example, inert diluents, for example lactose, granulating and disintegrating agents, for example calcium carboxymethylcellulose, microcrystalline cellulose or maize starch, binding agents, for example polyvinylpyrrolidone, and lubricating agents, for example magnesium stearate. The tablets may be uncoated or they may be coated by known techniques to increase stability or to mask unpalatable taste. They may also be formulated so as to delay disintegration and absorption in the gastrointestinal tract and thereby provide a sustained action over a longer period.

Compositions intended for oral use may also be presented as hard gelatine capsules containing the active ingredient only, or in admixture with an inert solid diluent, or they may be presented as soft gelatine capsules wherein the active ingredient is mixed with an oily medium.

Syrups and elixirs may be formulated with sweetening agents, and may also contain a demulcent, a preservative and flavouring and colouring agents.

Compositions intended for parenteral administration may be sterilised by conventional methods. The aqueous suspensions may contain the active ingredient in admixture with conventional pharmaceutical excipients, for example one or more suspending agents, dispersing agents or wetting agents. Similarly the oily solutions or suspensions may contain in addition to the active ingredient, for example one or more pharmaceutically acceptable vegetable or mineral oils, optionally together with a suitable anti-oxidant or emulsifying agent.

The pharmaceutical compositions of the invention may alternatively be in the form of a suppository or pessary intended for administration of the active ingredient per rectum or per vagina, respectively. Such compositions may be prepared by mixing the active ingredient with a conventional non-irritating excipient which is solid at ordinary temperatures but liquid at the body temperature and which will therefore melt in the body to release the active ingredients.

Many of the active ingredients defined hereinabove are known and have been previously described as possessing herbicidal properties in United Kingdom patent specification Ser. No. 1464248. We have now discovered that compounds of formula I surprisingly possess analgesic properties and in some cases, in addition, possess anti-inflammatory properties and/or are inhibitors of prostaglandin synthetase.

A preferred group of known active ingredients of the invention comprises the compounds of formula I shown in the following Table, together with the pharmaceutically acceptable base-addition salts thereof:

Table I

| Compound No. | $R^1$ | $R^2$ | $R^3$ |
|---|---|---|---|
| 1 | i-propyl | neo-pentyl | methyl |
| 2 | i-propyl | i-propyl | methyl |
| 3 | i-propyl | i-butyl | methyl |
| 4 | i-propyl | neo-pentyl | ethyl |
| 5 | i-propyl | sec-butyl | methyl |
| 6 | sec-butyl | neo-pentyl | methyl |
| 7 | i-propyl | n-butyl | methyl |
| 8 | i-propyl | ethyl | n-propyl |
| 9 | i-propyl | ethyl | methyl |
| 10 | n-butyl | n-butyl | methyl |
| 11 | cyclohexyl | n-propyl | methyl |
| 12 | cyclohexyl | methyl | methyl |

An especially preferred known active ingredient of the invention is 1-isopropyl-4-(N-acetyl)isopropylaminotetrahydro-1,3,5-triazine-2,6-dione (compound 2 in Table I), or a base-addition salt thereof as defined above.

Certain of the active ingredients of the invention are novel. According to a further feature of the invention, therefore, there is provided a novel 1,3,5-triazine-2,6-dione of the formula:

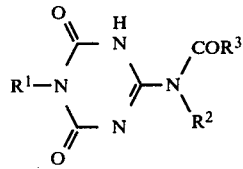

wherein $R^1$ is a $C_{1-6}$-alkyl radical or a $C_{3-6}$-cycloalkyl radical; $R^2$ is a $C_{1-4}$-alkyl radical bearing a $C_{1-4}$-alkoxy radical, a $C_{3-8}$-cycloalkyl or $C_{3-6}$-alkenyl radical, a $C_{5-10}$-alkyl radical wherein the linking α-carbon atom is secondary, or a phenyl or phenyl-$C_{1-4}$-alkyl radical optionally bearing an aromatic substituent selected from halogen atoms, $C_{1-4}$-alkyl and $C_{1-4}$-alkoxy radicals; and $R^3$ is a $C_{1-4}$-alkyl radical; or $R^1$ is an n-propyl or ethyl radical, $R^2$ is an n-propyl radical and, $R^3$ is a methyl radical; or $R^1$ is an isopropyl radical, $R^2$ is a 3,3-dimethylbutyl radical, and $R^3$ is a methyl radical; or a pharmaceutically acceptable base-addition salt thereof.

A particular value for $R^1$ when it is a $C_{1-6}$-alkyl radical is, for example, a methyl, ethyl, isopropyl, n-propyl or isobutyl radical; and when it is a $C_{3-6}$-cycloalkyl radical is, for example, a cyclohexyl radical.

A particular value for $R^2$ when it is a $C_{1-4}$-alkyl radical bearing a $C_{1-4}$-alkoxy radical is, for example, a 2-methoxy- or 2-ethoxy-ethyl radical; and when it is a $C_{3-6}$-alkenyl radical is, for example, an allyl or 2-methylallyl radical.

A particular value for $R^2$ when it is a $C_{3-8}$-cycloalkyl radical is, for example, a cyclopropyl, cyclobutyl, cyclopentyl, cyclohexyl or norbornyl radical; and when it is a $C_{5-10}$ radical wherein the linking α-carbon atom is secondary, is, for example, a pent-2-yl, pent-3-yl, hex-2-yl, hex-3-yl or hept-4-yl radical, of which latter values, a pent-3-yl radical is especially preferred.

A particular value for a phenyl-$C_{1-4}$-alkyl radical is, for example, a benzyl, 1-(phenyl)ethyl or 2-(phenyl)ethyl radical.

A particular value for an aromatic substituent which may be present when $R^2$ is a phenyl or phenyl-$C_{1-4}$-alkyl radical is, for example:

when it is a halogen substituent, a fluorine, chlorine or bromine atom;

when it is a $C_{1-4}$-alkyl substituent, a methyl radical; and when it is a $C_{1-4}$-alkoxy substituent, a methoxy radical.

Specific values for $R^2$ when it is an optionally substituted phenyl or phenyl-$C_{1-4}$-alkyl radical are, for example, phenyl, benzyl, 1-(phenyl)ethyl, 2-(phenyl)ethyl, 4-chlorophenyl, 4-methylphenyl, 3-methoxyphenyl and 4-chlorobenzyl radicals.

It is preferred that when $R^1$ and $R^2$ are both alkyl radicals, the radicals taken together number four or more carbon atoms.

A particular value for $R^3$ is, for example, a methyl, ethyl or n-propyl radical, of which a methyl radical is preferred.

Particular base-addition salts are those defined hereinbefore.

It will be apparent that within the above definition of novel compounds of formula I there are comprised various particular and distinct groups of novel compounds of the invention, namely those novel compounds of formula I, or pharmaceutically acceptable base-addition salts thereof, wherein one of $R^1$, $R^2$ and $R^3$ has one of the above defined particular or specific values, and the remainder of $R^1$, $R^2$ and $R^3$ have any of the above defined general, particular or specific values. However, specific groups of novel compounds of the invention which are of particular interest comprise those novel compounds of formula I wherein:

(a) $R^1$ is a straight chain $C_{1-6}$-alkyl radical, for example a methyl, ethyl or n-propyl radical, or $R^1$ is a $C_{3-6}$-cycloalkyl radical; and $R^2$ is a $C_{5-10}$-alkyl radical, wherein the linking α-carbon atom is secondary;

(b) $R^1$ is a $C_{1-6}$-alkyl or $C_{3-6}$-cycloalkyl radical; and $R^2$ is a pent-2-yl radical, or a $C_{6-10}$-alkyl radical wherein the linking α-carbon atom is secondary, for example a hex-3-yl or hept-4-yl radical;

(c) $R^1$ is a $C_{1-6}$-alkyl or $C_{3-6}$-cycloalkyl radical; and $R^2$ is a $C_{6-10}$-alkyl radical wherein the linking α-carbon atom is secondary;

(d) $R^1$ is a $C_{1-6}$-alkyl or $C_{3-6}$-cycloalkyl radical; and $R^2$ is a phenyl or phenyl-$C_{1-4}$-alkyl radical optionally substituted as defined hereinbefore;

(e) $R^1$ is a $C_{1-6}$-alkyl or $C_{3-6}$-cycloalkyl radical; and $R^2$ is a $C_{3-8}$-cycloalkyl radical; and (f) $R^1$ is a $C_{1-6}$-alkyl or $C_{3-6}$-cycloalkyl radical; and $R^2$ is a $C_{3-6}$-alkenyl radical or a $C_{1-4}$-alkyl radical bearing a $C_{1-4}$-alkoxy radical;

and in each group $R^3$ is a $C_{1-4}$-alkyl radical; together with the pharmaceutically acceptable base-addition salts thereof.

Preferred groups of novel compounds of formula I comprises those compounds wherein:

(a) $R^1$ is an isopropyl or n-propyl radical;

(b) $R^2$ is a pent-3-yl, hex-3-yl or cyclohexyl radical; or (c) $R^3$ is a methyl radical;

and, in each group, the remainder of $R^1$, $R^2$ and $R^3$ have any of the previously defined values; together with the pharmaceutically acceptable salt-addition salts thereof.

Yet further preferred groups of novel compounds of formula I comprise those compounds wherein $R^1$, $R^2$ and $R^3$ all have the values defined in (a), (b) and (c) immediately above; or wherein two of $R^1$, $R^2$ and $R^3$ have the values defined in (a), (b) or (c) immediately above, and the other of $R^1$, $R^2$ and $R^3$ has any of the values previously defined; together with the pharmaceutically acceptable base-addition salts thereof.

Specific novel compounds of formula I are described hereinafter in the Examples, and, of these, particularly preferred compounds are 1-isopropyl-4-(N-acetyl)cyclopropylamino-tetrahydro-1,3,5-triazine-2,6-dione, 1-isopropyl-4-[(N-acetyl)-pent-3-ylamino]-tetrahydro-1,3,5-triazine-2,6-dione and 1-isopropyl-4-(N-acetyl)-cyclohexylamino-tetrahydro-1,3,5-triazine-2,6-dione; and the pharmaceutically acceptable base-addition salts thereof.

The novel compounds of formula I may be obtained by any process applicable to the manufacture of analogous chemical compounds. Such processes are provided as a further feature of the invention and are illustrated by the following, wherein $R^1$, $R^2$ and $R^3$ have the meanings defined hereinbefore for novel compounds:

(a) acylating a compound of the formula:

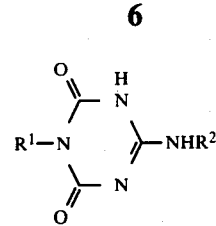

by reaction with an acylating agent derived from an acid of the formula $R^3CO_2H$.

A particularly suitable acylating agent is, for example, an acid halide, for example the acid chloride or bromide, the anhydride or a mixed anhydride with formic acid, derived from an acid of the formula $R^3CO_2H$.

The reaction may be carried out in the presence of a diluent or solvent, for example a hydrocarbon, for example toluene or xylene. An excess of the acylating agent is preferably used, and may itself serve as diluent or solvent. In either case the reaction is conveniently carried out at a temperature in the range, for example, 15°–150° C., and preferably, at an elevated temperature in the range, for example, 80°–150° C.

It will be appreciated that, when an anhydride is used as the acylating agent, the parent acid of the formula $R^3CO_2H$ is also formed, and may be conveniently removed by distillation.

The starting materials of formula II may be obtained, as described in the Examples, by reaction of an amine of the formula $R^2.NH_2$ with a 4-alkylthio-1,3,5-triazine derivative of the formula:

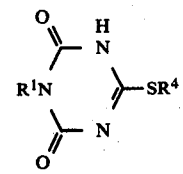

wherein $R^4$ is a $C_{1-4}$-alkyl radical, for example a methyl radical. The amine of the formula $R^2$—$NH_2$ is conveniently used in the form of its salt with a $C_{1-4}$-alkanoic acid, for example in the form of its acetate salt, and the reaction is preferably carried out at a temperature in the range, for example, 100°–250° C. A suitable solvent or diluent, for example dimethylformamide, may conveniently be used.

The 4-alkylthio compounds of formula III may be made by well known procedures for the synthesis of analogous 1,3,5-triazine-2,6-diones, for example as described in U.K. patent specification No. 1,435,585 or No. 1,397,888.

(b) Rearranging a compound of the formula:

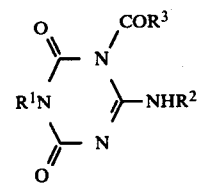

by the influence of heat.

The rearrangement is preferably carried out by heating at a temperature in the range, for example, 60°–200° C., and may optionally be carried out in the presence of a high boiling diluent or solvent, for example xylene.

The process is particularly suitable for the preparation of compounds of formula I wherein $R^3$ is a methyl radical and in which case the required starting materials of formula IV may be obtained by reaction of a compound of formula II with ketene, preferably at or near room temperature and in a diluent or solvent, for example methylene chloride. In many cases, it is convenient to prepare the compound of formula IV in situ, and use it without purification in process (b). The remaining starting materials of formula IV may be obtained in analogous manner using the appropriate substituted ketene of the formula $R^5.CH=C=O$ wherein $R^5$ is a $C_{1-3}$-alkyl radical.

The compounds of formula I are moderately acidic and react with weak bases, for example alkali metal hydrogen carbonates, to form the corresponding alkali metal salts.

Whereafter when a pharmaceutically acceptable base-addition salt is required a novel compound of formula I is reacted with a suitable base.

The analgesic properties of the compounds of formula I may be demonstrated in a standard test measuring the inhibition of writhing in mice induced by an intraperitoneal injection of acetylcholine, using the procedure of Hackett and Buckett (*European J. Pharmacology,* 1975, 30, 280). In general compounds of formula I show significant activity in this test at an oral dose of 50 mg./kg., or less, without any overt toxic effects at the active dose, the preferred compounds of formula I, for example the known compounds of Table I or, for example, the new compound 1-isopropyl-4-[(N-acetyl)-pent-3-ylamino]-tetrahydro-1,3,5-triazine-2,6-dione, show significant activity at an oral dose of 5 mg./kg. or much less.

In addition to analgesic properties, certain of the compounds of formula I possess anti-inflammatory properties which may be demonstrated using either or both of the following standard tests:

(a) Adjuvant induced arthritis in rats, using a similar procedure to that of B. B. Newbould (*British Journal of Pharmacology,* 1963, 21, 127);

(b) Carrageenin induced oedema in rats, using a similar procedure to that of C. A. Winter et alia [*Proceedings of the Society of Experimental Biology* (New York), 1962, 111, 544].

In general, compounds of formula I possessing anti-inflammatory properties show activity in either or both of the above tests at an oral dose of 50 mg./kg. or less, given as a daily dose for 14 days in test (a) or as a single dose in test (b), without overt toxic effects at the active dose.

Known compounds possessing good anti-inflammatory properties are, for example, compounds 1 and 10 of Table 1.

Novel compounds possessing good anti-inflammatory properties are, for example, 1-ethyl-4-(N-acetyl)-n-propylamino-, 1-n-propyl-4-(N-acetyl)-n-propylamino-, and 1-isopropyl-4-(N-acetyl)benzylamino-tetrahydro-1,3,5-triazine-2,6-dione.

Certain of the compounds of formula I also possess the property of inhibiting the enzyme prostaglandin synthetase. This property may be demonstrated in a standard in vitro test which involves the use of prostaglandin synthetase isolated from the ram seminal vesicle. Those compounds of formula I which inhibit prostaglandin synthetase, in general do so at an in vitro concentration of $10^{-3}M$ or less. Representative compounds of formula I which inhibit the enzyme prostaglandin synthetase are, for example, the known compounds numbered 1 and 4 in Table I, and the new compound 1-isopropyl-4-(N-acetyl)benzylamino-tetrahydro-1,3,5-triazine-2,6-dione.

It is know that inhibitors of prostaglandin synthetase, for example indomethacin or flufenamic acid, are clinically effective in the treatment of adverse conditions associated with abnormally high tissue levels of prostaglandins, for example dysmenorrhoea or menorrhagia, and in the treatment of painful inflammatory joint diseases, for example arthritis and osteoarthritis.

When used to produce the aforementioned pharmacological effects in warm blooded animals the compositions of the invention may be administered as follows:

(a) for analgesic effects, at a daily oral dose of for example, 0.1–25 mg./kg. of an active ingredient of formula I; (in humans this is equivalent to a total daily dose of active ingredient of, for example, 2.5–625 mg.);

(b) for anti-inflammatory effects, at a daily oral dose of, for example, 1–50 mg./kg. of an active ingredient of formula I possessing anti-inflammatory properties; (in humans this is equivalent to a total daily dose of active ingredient of, for example, 25–1250 mg.);

(c) to inhibit prostaglandin synthetase in vivo, at a daily dose of, for example, 1–50 mg./kg. of an active ingredient of formula I possessing the property of inhibiting prostaglandin synthetase; (in humans this is equivalent to a total daily dose of, for example, 25–1250 mg.).

The above total daily dose may conveniently be given in divided, but not necessarily equal doses and the active ingredient may be replaced by an equivalent amount of a suitable base-addition salt of a compound of formula I.

Convenient dosage unit forms of a composition of the invention contain, for example, 5, 10, 50, 100 or 200 mg. of an active ingredient of formula I or a base-addition salt thereof as defined hereinabove.

Compositions administered to obtain analgesic or anti-inflammatory effects, for example in the treatment of painful inflammatory joint disease such as arthritis and osteoarthritis, may also contain one or more agents known to be of value in the treatment of such conditions, for example an agent selected from the following:

anti-inflammatory and analgesic agents, such as acetyl salicylic acid, paracetamol, dexpropoxyphene, codeine, phenylbutazone, indomethacin, ibuprofen, ketoprofen and naproxen; anti-arthritic agents such as chloroquine, D-penicillamine and organo-gold derivatives; anti-inflammatory steriods, for example prednisolone; and uricosuric agents, for example probenecid.

The invention is illustrated, but not limited, by the following Examples in which yields, where given, are not to be construed as necessarily the maximum attainable:

EXAMPLE 1

1-Isopropyl-4-cyclopropylaminotetrahydro-1,3,5-triazine-2,6-dione (4.0 g.) was heated under reflux in acetic anhydride (50 ml.) for 3 hours. The excess of acetic anhydride was then removed in vacuo and the residue obtained was triturated with n-hexane containing a little ether. The brown solid which formed was separated and recrystallised from a mixture of carbon tetrachloride and petroleum ether (b.p. 60°–80° C.), giving 1-isopropyl-4-(N-acetyl)cyclopropylamino-tetrahydro-1,3,5-triazine-2,6-dione in 55% yield, m.p. 118°–119° C.

The starting material was obtained as follows:

1-Isopropyl-4-methylthiotetrahydro-1,3,5-triazine-2,6-dione (6.0 g.) (obtained as described in U.K. patent specification No. 1,435,585) and cyclopropylamine acetate (17.85 g.) were heated together and stirred at 150° C. for 3 hours. The mixture was then cooled and water (150 ml.) was added. The white solid which formed was collected, washed with water and dried to give 1-isopropyl-4-cyclopropylaminotetrahydro-1,3,5-triazine-2,6-dione, m.p. 237°–239° C.

EXAMPLE 2

In a similar manner to that described in Example 1 the following compounds of formula I wherein $R^3$ is a methyl radical were obtained in yields of 60–90% by acylating a compound of formula II with acetic anhydride:

| Compound No. | $R^1$ | $R^2$ | m.p. (°C.) |
|---|---|---|---|
| 1 | n-propyl | n-propyl | 117–118 |
| 2 | i-propyl | allyl | 108–109 |
| 3 | ethyl | n-propyl | 129–131 |
| 4 | i-propyl | 2-methylallyl | 96–97 |
| 5 | i-propyl | benzyl | 152–153 |
| 6 | i-propyl | phenyl | 199–201 |
| 7 | i-propyl | 2-methoxyethyl | 77–78 |
| 8 | i-propyl | 3,3-dimethylbutyl | 138–139 |

The necessary starting materials of formula II were obtained in an analogous manner to that described in Example 1 by reacting the appropriate 4-methylthio compound of formula III, wherein $R^4$ is a methyl radical, with an 8–10 molar excess of the appropriate amine as its acetate:

| Intermediate No. | $R^1$ | $R^2$ | m.p. °C. |
|---|---|---|---|
| 1 | n-propyl | n-propyl | 249–250 |
| 2 | i-propyl | allyl | 182–183 |
| 3 | ethyl | n-propyl | 248–250 |
| 4 | i-propyl | 2-methylallyl | 181–182 |
| 5 | i-propyl | benzyl | 251–254 |
| 6 | i-propyl | phenyl | 272–274 |
| 7 | i-propyl | 2-methoxyethyl | 98–100 |
| 8 | i-propyl | 3,3-dimethylbutyl | 216–218 |

EXAMPLE 3

Using a similar procedure to that described in Example 1 the following compounds of formula I wherein $R^1$ is an isopropyl radical and $R^3$ is a methyl radical were obtained in yields of 40–90%, by reacting a compound of formula II with an excess of acetic anhydride:

| Compound No. | $R^2$ | m.p. (°C.) |
|---|---|---|
| 9 | cyclohexyl | 129–131 |
| 10 | 1(phenyl)ethyl | syrup [Note (a)] |
| 11 | pent-3-yl | 85–88 |
| 12 | hex-3-yl | syrup [Note (b)] |
| 13 | hept-4-yl | syrup [Note (c)] |
| 14 | 4-chlorophenyl | 248–250 |
| 15 | 4-methylphenyl | 214–216 |

Notes: syrups were homogeneous by TLC analysis (SiO$_2$: acetic acid/ethyl acetate/toluene 2:80:18 v/v) and had the following characteristic NMR spectra [determined at 60 MH$_z$ in CDCl$_3$ solution using tetramethyl silane (TMS) as internal standard]:

(a), δ (ppm): 1.4, 1.5 [doublet (d), 6 protons, (C$\underline{H}_3$)$_2$CH]; 1.77, 1.9 [doublet (d), 3 protons, C$\underline{H}_3$CHPh]; 2.0 [singlet (s), 3 protons, N.COC$\underline{H}_3$]; 4.7–5.3 [multiplet (m), 1 proton. (CH$_3$)$_2$C$\underline{H}$]; 6.5–6.9 [quartet (q), 1 proton, CH$_3$C$\underline{H}$Ph]; 7.26 [singlet (s), 5 aromatic protons];

(b), δ (ppm) (100 MH$_z$): 0.86–1.0 [t, 6 protons, C$\underline{H}_3$(CH$_2$)$_2$CHCH$_2$C$\underline{H}_3$]; 1.15–1.35 (m, 2 protons, CH$_3$C$\underline{H}_2$CH$_2$CHCH$_2$CH$_3$); 1.42–1.50 [d, 6 protons, (C$\underline{H}_3$)$_2$CH]; 1.65–2.35 (m, 4 protons, CH$_3$CH$_2$C$\underline{H}_2$CHC$\underline{H}_2$CH$_3$); 2.43 (s, 3 protons, N.COCH$_3$); 4.05–4.40 [m, 1 proton, CH$_3$(CH$_2$)$_2$C$\underline{H}$CH$_2$CH$_3$]; 4.8–5.2 [m, 1 proton, (CH$_3$)$_2$C$\underline{H}$]; (c), δ (ppm): 0.7–1.1 (t, 6 protons, C$\underline{H}_3$CH$_2$CH$_2$CH-); 1.1–1.7 (m, 4 protons, CH$_3$C$\underline{H}_2$CH$_2$CH); 1.42–1.53 [d, 6 protons, (C$\underline{H}_3$)$_2$CH]; 1.77–2.35 (m, 4 protons, CH$_3$CH$_2$C$\underline{H}_2$CH); 2.47 (s, 3 protons, N.COCH$_3$); 4.05–4.60 (m, 1 proton, CH$_3$CH$_2$CH$_2$C$\underline{H}$); 4.73–5.40 [m, 1 proton, (CH$_3$)$_2$C$\underline{H}$].

The necessary starting materials of formula II were obtained in an analogous manner to that described in Example 1 by reacting 1-isopropyl-4-methylthio-tetrahydro-1,3,5-triazine-2,6-dione with a 1.5–2.0 molar excess of the appropriate amine as its acetate:

| Intermediate No. | $R^2$ | m.p. (°C.) |
|---|---|---|
| 9 | cyclohexyl | 253–258 |
| 10 | 1(phenyl)ethyl | 169–171 |
| 11 | pent-3-yl | 253–256 |
| 12 | hex-3-yl | syrup [Note (a)] |
| 13 | hept-4-yl | syrup [Note (b)] |
| 14 | 4-chlorophenyl | 248–250 |
| 15 | 4-methylphenyl | 286–288 |

Notes: syrups were homogeneous by TLC analysis (SiO$_2$: acetic acid/ethyl acetate/toluene; 2:35:63 v/v) and had the following characteristic NMR spectra [determined at 60 MH$_z$ in CDCl$_3$ solution using TMS as internal standard]:

(a), δ (ppm): 0.77–1.17 (t, 6 protons, C$\underline{H}_3$CH$_2$CH$_2$.CHCH$_2$C$\underline{H}_3$); 1.42 and 1.52 [δ,6 protons, (C$\underline{H}_3$)$_2$CH]; 1.17–2.07 (m, 6 protons, CH$_3$C$\underline{H}_2$CH$_2$.CHCH$_2$C$\underline{H}_3$); 3.62–4.32 [m(broad), 1 p, CH$_3$CH$_2$CH$_2$.C$\underline{H}$CH$_2$CH$_3$]; 4.72–5.37 [m, 1 proton, (CH$_3$)$_2$C$\underline{H}$]; 8.17 [d(broad), 1 proton, NH];

(b) δ (ppm): 0.7–9.1 (t, 6 protons, C$\underline{H}_3$CH$_2$CH$_2$CH); 1.1–1.9 (m, 8 protons, CH$_3$C$\underline{H}_2$C$\underline{H}_2$CH); 1.4–1.53 [d, 6 protons, (C$\underline{H}_3$)$_2$CH]; 3.6–4.3 [m(broad), 1 proton, CH$_3$CH$_2$CH$_2$C$\underline{H}$]; 4.7–5.3 [m, 1 proton, (CH$_3$)$_2$C$\underline{H}$].

EXAMPLE 4

A suspension of 1-isopropyl-4-(N-acetyl)cyclohexylamino-tetrahydro-1,3,5-triazine-2,6-dione (10 mM) in a mixture of water (50 ml.) and 1,2-dimethoxyethane (10 ml.) was prepared. Sodium hydrogen carbonate (10 mM.) in water (50 ml.) was then added to the stirred suspension. After 1 hour at room temperature the solution was filtered and the filtrate evaporated in vacuo. The solid residue was then triturated with a little 1,2-dimethoxyethane to give the sodium salt of 1-isopropyl-4-(N-acetyl)cyclohexylamino-tetrahydro-1,3,5-triazine-2,6-dione in essentially quantitative yield as a white solid, having a satisfactory microanalysis.

EXAMPLE 5

A mixture of 50 parts by weight of 1-isopropyl-4-(N-acetyl)isopropylaminotetrahydro-1,3,5-triazine-2,6-dione, 27 parts by weight of lactose, and 20 parts by weight of maize starch was thoroughly stirred, and a paste formed from 2 parts by weight of maize starch and 40 parts by weight of water was added and thoroughly mixed. The resulting mass was passed through a 16-mesh screen, dried at 60° C. to constant weight and then passed through a 20 mesh screen. 1 Part by weight of magnesium stearate was added to the granules thus obtained and the mixture was compressed by conventional means, into tablets containing 5, 10, 50, 100 and 200 mg. of active ingredient, suitable for oral administration for therapeutic purposes.

EXAMPLE 6

A mixture of 50 parts by weight of 1-isopropyl-4-(N-acetyl)-isopropylaminotetrahydro-1,3,5-triazine-2,6-dione, 33 parts by weight of calcium phosphate, 10 parts by weight of microcrystalline cellulose and 4 parts by weight of calcium carboxymethylcellulose was thoroughly stirred and a paste formed from 2 parts by weight of polyvinylpyrrolidone and 40 parts by weight of water and was added and thoroughly mixed. The resulting mass was passed through a 16-mesh screen, dried at 60° C. to constant weight and then passed through a 20-mesh screen. 1 Part by weight of magnesium stearate was added to the granules thus obtained and the mixture was compressed by conventional means into tablets containing 5, 10, 50, 100 and 200 mg. of active ingredient, suitable for oral administration for therapeutic purposes.

EXAMPLE 7

The process described in Example 5 or 6 was repeated but the active ingredient was replaced by a known compound of formula I as defined hereinbefore, for example compound 1 or any compound from 3–12 in Table I. There were thus similarly obtained tablets containing 5, 10, 50, 100 and 200 mg. of the appropriate active ingredient, suitable for oral administration for therapeutic purposes.

EXAMPLE 8

The process described in Example 5 or 6 was repeated except that the active ingredient was replaced by the new compound 1-isopropyl-4-(N-acetyl)cyclopropylaminotetrahydro-1,3,5-triazine-2,6-dione. There were thus obtained tablets containing 5, 10, 50, 100 and 200 mg. of active ingredient suitable for oral administration for therapeutic purposes.

In a similar manner the active ingredient in the process of Example 5 or 6 may be replaced by a new compound of formula I, for example as described in Example 2, to give tablets suitable for oral administration for therapeutic purposes.

EXAMPLE 9

A mixture of lactose (130 parts by weight), 1-isopropyl-4-(N-acetyl)isopropylamino-tetrahydro-1,3,5-triazine-2,6-dione (50 parts) and maize starch (16 parts) was stirred thoroughly and a paste formed from maize starch (2 parts) and water (40 parts) was added. The mixture was stirred thoroughly and then sieved and dried at 60° C. to constant weight in conventional manner. Magnesium stearate (2 parts) was then added to the granules obtained, and the resultant mixture was compressed using known procedures into tablets, weighing 200 mg. and containing 50 mg. of active ingredient, suitable for oral administration for therapeutic purposes.

By similar procedure, tablets containing 50 mg. of any other known compound of formula I described in Table I hereinbefore, or a salt thereof, may be obtained suitable for oral administration for therapeutic purposes.

EXAMPLE 10

Using the same overall procedure as described in Example 9, tablets containing 50 mg. of 1-isopropyl-4-(N-acetyl)cyclohexylamino-tetrahydro-1,3,5-2,6-dione or any other novel compound or salt thereof described in any of Examples 1–4 may be obtained, suitable for oral administration for therapeutic purposes.

What is claimed is:

1. A pharmaceutical composition which comprises as active ingredient a 1,3,5-triazine-2,6-dione of the formula:

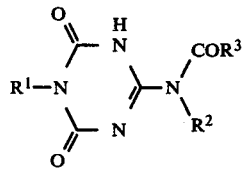

wherein $R^1$ is a $C_{1-6}$-alkyl or $C_{3-6}$-cycloalkyl radical; $R^2$ is a $C_{1-10}$-alkyl radical, a $C_{1-4}$-alkyl radical bearing a $C_{1-4}$-alkoxy radical, a $C_{3-8}$-cycloalkyl or $C_{3-6}$-alkenyl radical, or a phenyl or phenyl-$C_{1-4}$-alkyl radical optionally bearing an aromatic substituent selected from halogen atoms, $C_{1-4}$-alkyl and $C_{1-4}$-alkoxy radicals; and $R^3$ is a $C_{1-4}$-alkyl radical; or a pharmaceutically acceptable base-addition salt thereof; together with a pharmaceutically acceptable diluent or carrier.

2. A composition as claimed in claim 1 wherein $R^1$ is a methyl, ethyl, n-propyl, isopropyl, n-butyl, isobutyl, sec-butyl, neopentyl, cyclopropyl, cyclobutyl, cyclopentyl or cyclohexyl radical; $R^2$ is a methyl, ethyl, n-propyl, n-butyl, n-pentyl, isopropyl, isobutyl, sec-butyl, pent-2-yl, pent-3-yl, neopentyl, hex-2-yl, hex-3-yl, hept-4-yl, allyl, 2-methylallyl, cyclopropyl, cyclobutyl, cyclopentyl, cyclohexyl, norbornyl, 2-methoxyethyl or 2-ethoxyethyl radical, or a phenyl, benzyl, 1-(phenyl)ethyl or 2-(phenyl)ethyl radical optionally bearing an aromatic substituent selected from fluorine, chlorine and bromine atoms, and methyl and methoxy radicals; and $R^3$ is a methyl, ethyl or n-propyl radical.

3. A composition as claimed in claim 1 wherein $R^2$ is an isopropyl, sec-butyl, pent-2-yl, allyl, 2-methylallyl, cyclopropyl, cyclobutyl, cyclopentyl, cyclohexyl, norbornyl, 2-methoxyethyl, 2-ethoxyethyl, phenyl, benzyl, 1-(phenyl)ethyl, 2-(phenyl)ethyl, 4-chlorophenyl, 4-methylphenyl, 3-methoxyphenyl, or 4-chlorobenzyl radical.

4. A composition as claimed in claim 1 wherein $R^3$ is a methyl radical.

5. A composition as claimed in claim 1 wherein $R^1$ and $R^2$ are both alkyl radicals as defined hereinbefore and which taken together number four or more carbon atoms.

6. A composition as claimed in claim 1 wherein the active ingredient is one of the compounds number 1–12 in Table I hereinbefore, or a pharmaceutically acceptable base-addition salt thereof.

7. A composition as claimed in claim 1 wherein the base-addition salt of the active ingredient of formula I is an alkali metal or alkaline earth metal salt, aluminium salt, copper salt or a complex therewith, or a salt with an organic base affording a pharmaceutically acceptable cation.

8. A composition as claimed in claim 1 which is in a form suitable for oral, parenteral, rectal or vaginal administration.

9. An oral composition as claimed in claim 8 which is in the form of a tablet, capsule, syrup or elixir.

10. A method of producing an analgesic effect in a warm-blooded animal requiring such treatment which comprises administering to said animal an effective amount of an active ingredient of formula I as defined in claim 1.

* * * * *